United States Patent [19]
Storni et al.

[11] Patent Number: 4,697,020
[45] Date of Patent: Sep. 29, 1987

[54] DERIVATIVES OF 2,4-THIAZOLIDINEDIONE

[75] Inventors: Angelo Storni, Allschwil; Alex Meisels, Basel, both of Switzerland

[73] Assignee: Ciba-Geigy Corporation, Ardsley, N.Y.

[21] Appl. No.: 918,584

[22] Filed: Oct. 9, 1986

Related U.S. Application Data

[60] Continuation of Ser. No. 754,566, Jul. 12, 1985, abandoned, which is a division of Ser. No. 393,907, Jun. 30, 1982, abandoned, which is a continuation of Ser. No. 45,158, Jun. 4, 1979, abandoned, which is a continuation of Ser. No. 639,025, Dec. 9, 1975, abandoned, which is a continuation of Ser. No. 441,680, Feb. 11, 1974, abandoned.

[30] Foreign Application Priority Data

Feb. 13, 1973 [CH] Switzerland .......................... 2016/73
Nov. 13, 1973 [CH] Switzerland ....................... 15960/73
Nov. 13, 1973 [CH] Switzerland ....................... 15961/73

[51] Int. Cl.$^4$ .................. C07D 233/28; A61K 31/425
[52] U.S. Cl. .................................... 548/184; 548/182; 548/183
[58] Field of Search ....................... 548/182, 184, 183

[56] References Cited

U.S. PATENT DOCUMENTS 3,699,116 10/1972 Meisels ............................ 260/306.7

FOREIGN PATENT DOCUMENTS 810894 8/1974 Belgium .

Primary Examiner—Nicholas S. Rizzo
Attorney, Agent, or Firm—Irving M. Fishman

[57] ABSTRACT

Compounds of the class of 2,2'-azines of 2,4-thiazolidinediones which are substituted in at least one of the 3-positions by allyl, 1-methylallyl, 2-methylallyl or 2-propynyl and in at least one of the 5-positions by hydroxy, and may further contain methyl groups in the remaining 3-position and in the 5-positions, and the corresponding tautomeric 1-[[4-oxo-2-thiazolidinylidene]amino]-5-hydroxy-2-thiohydantoins and 5,5'-dihydroxy-2,2'-dithio-1,1'-bihydantoins have valuable pharmacological properties. In particular, they inhibit the growth of tumours, while their toxicity is low in comparison with their tumour-inhibiting effectiveness. A specific embodiment is the 2,2'-azine of 3-(2-methylallyl)-5-methyl-2,4-thiazolidinedione and of 3-methyl-5-hydroxy-2,4-thiazolidinedione.

4 Claims, No Drawings

DERIVATIVES OF 2,4-THIAZOLIDINEDIONE

This application is a continuation of application Ser. No. 754,566, filed July 12, 1985, now abandoned; which is a divisional of application Ser. No. 393,907, filed June 30, 1982, now abandoned; which is a continuation of application Ser. No. 045,158; filed June 4, 1979, now abandoned; which is a continuation of application Ser. No. 639,025, filed Dec. 9, 1975, now abandoned; which is a continuation of application Ser. No. 441,680, filed Feb. 11, 1974, now abandoned; which in turn claims priority under 35 USC 119 of Swiss application Nos. 15961/73, filed Nov. 13, 1973, 15960/73, filed Nov. 13, 1973, and 2016/73, filed Feb. 13, 1973.

DETAILED DESCRIPTION

The present invention relates to processes for the preparation of new azines and their tautomers having valuable pharmacological properties, to these compounds as new substances, and to therapeutic preparations containing them.

The new azines and their tautomers according to the invention correspond to the general formula I

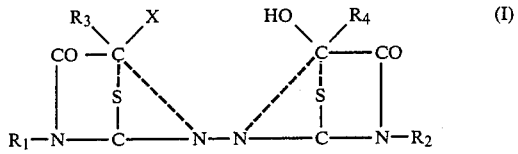

wherein
one of the symbols $R_1$ and $R_2$ represents allyl, 1-methylallyl, 2-methylallyl or 2-propynyl, and the other likewise one of these groups, or methyl,
$R_3$ and $R_4$ each independently represent hydrogen or methyl, and
X represents hydrogen or hydroxyl, and wherein in the right half of the formula bonds corresponding to the dotted lines or to the dashed lines are present, and
in the left half of the formula, in the case where X denotes hydrogen, bonds corresponding to the dotted lines or, in the case where X represents hydroxyl, corresponding to the dotted lines or to the dot-dash lines are present.

The invention relates also to processes for the preparation of one or more tautomeric compounds of the general formula I, the said processes comprising
(a) the allowing of an acid medium to act on an azine of the general formula II

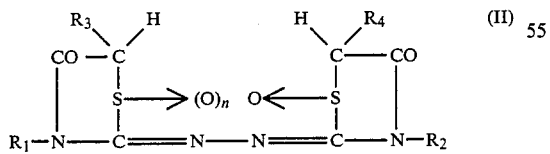

wherein
n represents 0 or 1,
and $R_1$, $R_2$, $R_3$ and $R_4$ have the meanings given under formula I; or
(b) the reaction of a compound of the general formula III

$$R_4-CO-CO-O-R_5 \quad \text{(III)}$$

wherein
$R_5$ represents hydrogen or lower alkyl, and
$R_4$ has the meaning given under formula I,
with a thiosemicarbazone of the general formula IV

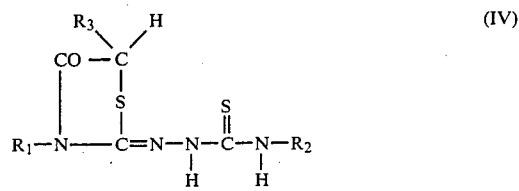

wherein $R_1$, $R_2$ and $R_3$ have the meanings given under formula I, or with the, at most, semimolar amount of a 2,5-dithiobiurea of the general formula V

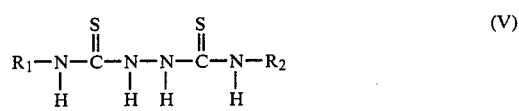

wherein $R_1$ and $R_2$ have the meanings given under the general formula I, optionally the separation from the direct reaction product obtained according to (a) or (b) of one or more tautomeric compounds of the general formula I, particularly a compound of the general formula Ia

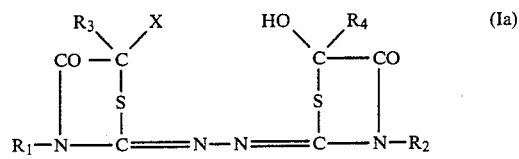

and/or, depending on the meaning of X, either a compound of the general formula Ib

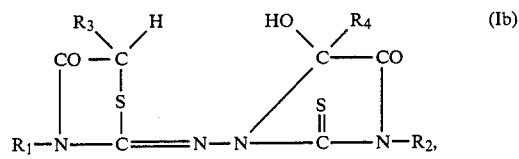

or a compound of the general formula Ic

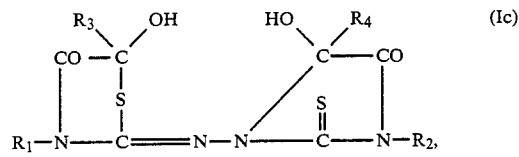

or a compound of the general formula Id

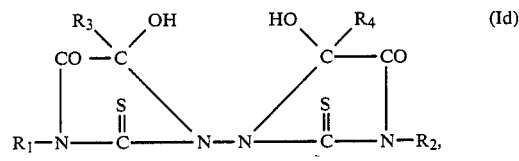

in which formulae the symbols $R_1$, $R_2$, $R_3$, $R_4$ and, if present, X have the meanings given under formula I; and (c) optionally the conversion of a single compound embraced by the general formula I and not corresponding to the above given general formula Ib or Id, or of a mixture of tatuomeric compounds embraced by the general formula I, by heating in the presence or absence of a solvent or diluent optionally containing an acid, into a compound of the general formula Ib or Id, or into a mixture containing an appreciable amount of this compound.

The rearrangement of compounds of the general formula II into a tautomeric compound or into a mixture of several such compounds of the general formula I is effected, for example, in an acid medium comprising an aqueous mineral acid, e.g. 1N to 7N, preferably 5N, hydrochloric acid, and a water-miscible or a readily water-soluble organic solvent, such as, e.g. dimethyl sulphoxide. The reaction temperature is between ca. 10° and 60° C.; the rearrangement is preferably performed at room temperature. Depending on the temperature, the duration of the reaction is ca. 2 to 72, preferably ca. 5 to 48, hours.

In the starting materials of the general formula III for process (b), the lower alkyl $R_5$ preferably contains 1 to 4 carbon atoms and is, e.g. methyl, ethyl, propyl, isopropyl, butyl or tert.butyl. The reaction of compounds of the general formula III, e.g. of glyoxylic acid or its tert.butyl ester or pyruvic acid or its tert.butyl ester, with thiosemicarbazones of the general formula IV, also with 2,5-dithiobiureas of the general formula V, is preferably performed at a temperature of between ca. 60° and 140° C., and usually in an inert organic solvent, e.g. in a hydrocarbon such as benzene or toluene, in a halogenated hydrocarbon such as chloroform, in a cyclic ether such as dioxane or tetrahydrofuran, or in a lower alkanol such as methanol, ethanol or tert.butanol. The reactions are performed, in particular, at the boiling temperature of the employed solvent, or, if necessary, also above this temperature in a closed vessel. The glyoxylic acid and esters thereof can also be used in the form of their hydrates. Especially in such cases it is possible, if desired, to accelerate the reaction by use of a water separator.

The separation of various tautomeric compounds of the general formula I can be performed, for example, by chromatography, e.g. on silica gel; but, by virtue of their good crystallisability, the compounds of the general formula Ia can be separated from the reaction mixtures containing them in most cases also by fractional crystallisation.

For their part, the azines of the general formula II are new compounds. They can be prepared, for example, by mono- or dioxidation of corresponding azines with non-oxidised sulphur atoms, which azines correspond to the general formula VI

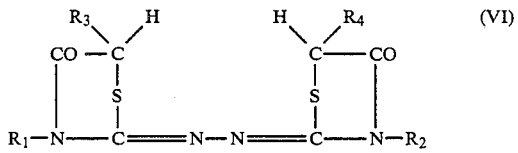

wherein $R_1$, $R_2$, $R_3$ and $R_4$ have the meanings given under formula I. Of the azines of the general formula VI, some are described in the Swiss Patent Specifications Nos. 458 358, 458 359, 458 360, 459 216 and 511 878; in the French Patent Specification No. 1,498,000; in the English Patent Specifications Nos. 1,122,604 and 1,325,061; and in the U.S. Pat. No. 3,699,116. Further compounds can be prepared by methods analogous to those for the known compounds.

The mono- and dioxidation of the azines of the general formula VI known from the aforementioned patent specifications, as well as of analogous new azines of this formula, to give starting materials of the general formula II are performed preferably by means of the ca. equimolecular amount and ca. bimolecular amount, respectively, of a peroxy acid, such as, e.g. peroxybenzoic acid and, in particular, m-chloroperoxybenzoic acid or monoperoxyphthalic acid, in an inert organic solvent, e.g. in a halogenated hydrocarbon, especially in methylene chloride or in chloroform, at a temperature of between ca. $-20°$ and $+50°$ C., or at the boiling temperature of the employed solvent if this should be lower than 50° C., preferably with reaction times of ca. 1 to 24 hours.

Of the thiosemicarbazones of the general formula IV required as starting materials for process (b), some are described, as starting materials for corresponding azines of the general formula VI, in the patent specifications mentioned under this formula; special reference is made in this connection to the Swiss Patent Specification No. 511 878, the English Patent Specification No. 1,325,061, as well as to the U.S. Pat. No. 3,699,116. The preparation of a thiosemicarbazone embraced by the general formula IV is also described in the Swiss Patent Specification No. 511 877 and in the English Patent Specification No. 1,301,555; and further thiosemicarbazones embraced by formula IV can be prepared by methods analogous to those for the known representatives.

Of the 2,5-dithio-biureas of the general formula V required as further starting materials for process (b), some are described in the Swiss Patent Specification No. 459 216, in the French Patent Specification No. 1,498,008, in the British Patent Specification No. 1,122,604, as well as in the U.S. Pat. No. 3,699,116; and further ones can be prepared by methods analogous to those for the known compounds.

The isomerisation of compounds of the general formula Ia, as well as of further tautomeric compounds of the general formula I, or of mixtures of such compounds, into compounds of the general formula Ib or Id, or into mixtures containing a higher proportion of these compounds, is performed, for example, by boiling of the respective compounds or mixtures in a polar solvent, e.g. in dimethyl sulphoxide, or in a lower alkanol, such as, e.g. methanol, ethanol, isopropanol or butanol, if necessary with the addition of an acid, e.g. an aqueous mineral acid, such as moderately diluted hydrochloric acid; or by heating in a nonpolar solvent to higher tempertures.

As intermediate stages of isomerisation, there are to be assumed, with any chosen meaning of X, monocyclic tautomers of the following general formula VIIa, and, with the presence of hydroxyl as X, also non-cyclic or monocyclic tautomers of the following general formulae VIIb and VIIc

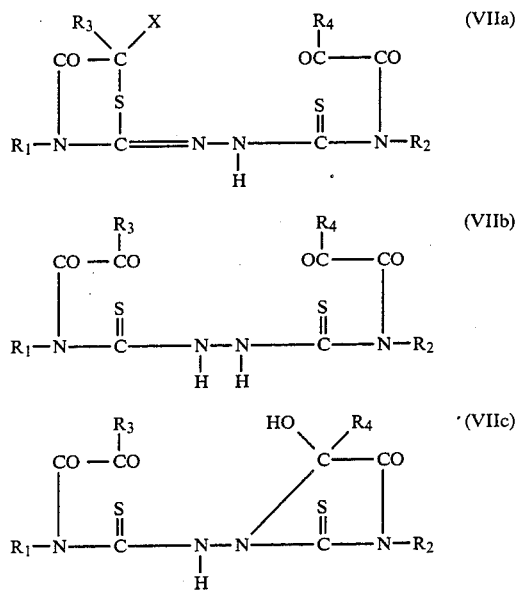

In these formulae, $R_1$, $R_2$, $R_3$, $R_4$ and, where present, X have the meanings given under formula I.

The present invention relates also to such modifications of the processes mentioned under (a), (b) and (c) and of their preliminary stages, whereby a process is interrupted at some stage, or whereby a compound occurring as an intermediate at some stage is taken as the starting product and the uncompleted stages are performed, or whereby a starting material is formed under the reaction conditions or, optionally, is used in the form of a salt.

The new azines and their tautomers corresponding to the general formula I possess valuable pharmacological properties. In particular, they inhibit the growth of tumours, as can be shown in animal tests with oral, subcutaneous and intramuscular administration; for example, in the case of the Walker sarcoma in the rat and in the case of mastocarcinoma in the rat induced by dimethylbenzanthracene. At the same time the toxicity of the compounds of the general formula I is low but their tumour-inhibiting effectiveness high, so that the compounds of the general formula I can be used for the treatment of neoplastic diseases in warm-blooded animals.

In the course of clinical testing of the 2,2'-azine of 3-methyl-2,4-thiazolidinedione and 3-(2-methyl-allyl)-5-methyl-2,4-thiazolidinedione a mixture of metabolic substances was isolated, which mixture was more hydrophilic than the test substance, showed an ultraviolet absorption spectrum similar to that of the latter and also had cytotoxic effects. The structure of specific compounds in the metabolite mixture was not identified. In the present invention, substantially pure compounds of uniform structure and improved activity over that of the above mentioned metabolic mixture are provided.

The invention concerns, in particular, compounds of the general formula I wherein X represents hydroxyl, or preferably hydrogen, one of the symbols $R_1$ and $R_2$ represents the allyl or 2-methylallyl group, and the other likewise one of these two groups, or preferably a methyl group, whilst $R_3$ and $R_4$ have the meanings defined under formula I. Among the various tautomeric groups of compounds embraced by the general formula I, the ones of particular interest, because of the ease with which they can be isolated, are those of the more limited general formulae Ia, Ib and Id. Compounds of the general formula I wherein $R_3$ and $R_4$ represent at the same time either hydrogen or methyl groups, and X is hydrogen or preferably hydroxyl, while $R_1$ and $R_2$ have the meanings given under the general formula I or preferably the aforementioned more limited meaning, are characterised, in particular, by the simplicity with which they can be prepared. Of particular importance, however, are the tautomeric compounds of the general formula I wherein one of the symbols $R_1$ and $R_2$, preferably $R_1$, represents the 2-methylallyl group and the other, preferably $R_2$, the methyl group, and the ring substituted in the 3-position by a 2-methylallyl group contains in the 5-position a methyl group as $R_3$ or $R_4$, while the other ring contains in the 5-position hydrogen as $R_4$ or $R_3$, and X represents the hydroxyl group or preferably hydrogen, such as the 2,2'-azine of 3-(2-methylallyl)-5-methyl-2,4-thiazolidinedione and of 3-methyl-5-hydroxy-2,4-thiazolidinedione, and 1-[[3-(2-methylallyl)-4-oxo-5-methyl-2-thiazolidinylidene]amino]-3-methyl-5-hydroxy-2-thiohydantoin, as well as further compounds given in the examples, such as 2,2'-azine of 3-methyl-5-hydroxy-2,4-thiazolidinedione and of 3-(2-methylallyl)-5-hydroxy-2,4-thiazolidinedione, and 3-allyl-3'-methyl-5,5'-dihydroxy-2,2'-dithio-1,1'-bihydantoin.

The daily doses suitable for the treatment of neoplasia of azines and their tautomers corresponding to the general formula I are in the case of mammals between 1 mg and 150 mg per kg of body weight; and, within this range, generally lower when administered parenterally, especially intramuscularly or subcutaneously, than when administered orally. The azines and their tautomers corresponding to the general formula I are administered orally or rectally preferably in the form of dosage units such as tablets, dragées, capsules or suppositories; and parenterally in the form of injection solutions, emulsions or suspensions.

Dosage units for oral administration contain as active substances preferably between 20% and 90% of an azine or of one of its tautomers corresponding to the general formula I. The dosage units are prepared by the mixing of the active substance with, e.g. solid pulverulent carriers such as lactose, saccharose, sorbitol, mannitol; starches such as potato starch, maize starch or amylopectin, also laminaria powder or citrus pulp powder; and cellulose derivatives or gelatine, optionally with the addition of lubricants, magnesium or calcium stearate or polyethylene glycols; and the subsequent pressing of the mixture into the form of tablets or dragée cores. The last-mentioned are coated, for example, with concentrated sugar solutions, which may also contain, e.g. gum arabic, talcum and/or titanium dioxide; or with a lacquer dissolved in readily volatile organic solvents or solvent mixtures. Colouring agents can be added to these coatings, e.g. for identification of the various doses of active substance.

Instead of the azines and their tautomers corresponding to the general formula I being administered in the form of dosage units, they can be administered orally as such in a suitable crystal or particle size; e.g. mixed with foodstuffs, particularly in the form of milk shakes.

Suitable dosage units for rectal administration are, e.g. suppositories consisting of a combination of an azine or of one of the tautomers thereof corresponding to the general formula I with a neutral fatty foundation substance; or gelatine rectal capsules containing a combination of the active substance with polyethylene glycols.

Applicable dosage units for parenteral administration are ampoules containing aqueous dispersions (prepared by means of suitable solubility-promoting agents and/or emulsifiers) of azines or their tautomers corresponding to the general formula I.

The azines of the general formula II used as starting materials have valuable pharmacological properties similar to those of compounds of the general formula I. In particular, they likewise inhibit the growth of tumours, as can be shown in animal tests with subcutaneous, oral and intramuscular administration; for example, in the case of the Walker sarcoma in the rat and in the case of mastocarcinoma induced by dimethylbenzanthracene in the rat. They too have low toxicity combined with a high level of effectiveness in inhibiting the growth of tumours, so that they likewise can be used for the treatment of neoplastic diseases in warm-blooded animals.

Of particular importance are azines of the general formula II wherein one of the symbols $R_1$ and $R_2$ represents the allyl or 2-methylallyl group, and the other likewise one of these two groups or preferably a methyl group, while $R_3$, $R_4$ and n have the meanings given under formula I and II; and, in particular, the azines of the general formula I wherein one of the symbols $R_1$ and $R_2$, preferably $R_1$, represents the 2-methylallyl group and the other, preferably $R_2$, the methyl group, and the ring substituted in the 3-position by a 2-methylallyl group contains in the 5-position a methyl group as $R_3$ or $R_4$, while the other ring contains in the 5-position hydrogen as $R_4$ or $R_3$, and n is 0 or 1, such as the 2,2'-azine of 3-(2-methylallyl)-5-methyl-2,4-thiazolidinedione and of 3-methyl-2,4-thiazolidinedione-1-oxide, and the 2,2'-azine of 3-(2-(methylallyl)-5-methyl-2,4-thiazolidinedione-1-oxide and of 3-methyl-2,4-thiazolidinedione-1-oxide.

The doses and modes of administration are in line with those for the compounds of the general formula I.

The following examples illustrate the preparation of azines and their tautomers corresponding to the general formula I, as well as of starting materials not hitherto known. The examples, however, are not intended in any way to limit the scope of the invention. The temperatures are expressed in degrees Centigrade.

EXAMPLE 1

1.3 g (5.0 mMol) of 3-methyl-2,4-thiazolidinedione-2-[4-(2-methylallyl)-3-thiosemicarbazone] and 0.50 g (5.5 mMol) of glyoxylic acid hydrate are dissolved in 20 ml of chloroform, and refluxed with stirring for 2 hours. The precipitated 2,2'-azine of 3-methyl-2,4-thiazolidinedione and of 3-(2-methylallyl)-5-hydroxy-2,4-thiazolidinedione is filtered off, successively washed with 10 ml of water, 5 ml of ethanol and 5 ml of ether, and dried for 4 hours at 50° in a water-jet vacuum. The substance obtained melts at 197°–198°.

EXAMPLE 2

27.2 g (0.10 Mol) of 3-(2-methylallyl)-5-methyl-2,4-thiazolidinedione-2-(4-methyl-3-thiosemicarbazone) and 10.1 g (0.11 Mol) of glyoxylic acid hydrate are refluxed in 300 ml of benzene with stirring for 90 minutes with the use of a water separator. After 15 minutes, an amount of 3.5 ml of water has already been separated. The hot reaction solution is subsequently decanted from a small amount of a yellow greasy residue and allowed to slowly cool. The 2,2'-azine of 3-(2-methylallyl)-5-methyl-2,4-thiazolidinedione and of 3-methyl-5-hydroxy-2,4-thiazolidinedione which has crystallised out is filtered off with suction, then washed with 100 ml of ether, and dried for 4 hours at 50° in a water-jet vacuum; M.P. 147°–148°.

The whole filtrate is washed twice with 50 ml of water each time, dried over sodium sulphate and concentrated by evaporation. The slightly yellowish, viscous oil (15 g) remaining behind is chromatographed on 450 g of silica gel. The first ether fractions elute 2,2'-azine of 3-(2-methylallyl)-5-methyl-2,4-thiazolidinedione and of 3-methyl-5-hydroxy-2,4-thiazolidinedione; there then follow a number of mixed fractions and the late ether fractions elute 1-[[3-(2-methylallyl)-4-oxo-5-methyl-2-thiazolidinylidene]-amino]-3-methyl-5-hydroxy-2-thiohydantoin, M.P. 136°–139°.

EXAMPLE 3

24.3 g (0.10 Mol) of 3-methyl-2,4-thiazolidinedione-2-[4-(2-propynyl)-3-thiosemicarbazone] and 9.1 g (0.10 Mol) of glyoxylic acid hydrate are refluxed in 500 ml of chloroform for 30 minutes with stirring and with the use of a water separator. After cooling, the product which has crystallised out is filtered off with suction and washed with 50 ml of chloroform. The filter residue is recrystallised once from methylene chloride to obtain the pure 2,2'-azine of 3-methyl-2,4-thiazolidinedione and of 3-(2-propynyl)-5-hydroxy-2,4-thiazolidinedione, M.P. 255° (decomp.).

The starting material can be prepared as follows:

(a) 29.4 g (0.20 Mol) of 3-methyl-2,4-thiazolidinedione-2-hydrazone and 20 g (0.206 Mol) of 2-propynyl-isothiocyanate are dissolved in 500 ml of benzene, and the solution heated to 60° for 2 hours. After cooling, the 2,4-thiazolidinedione-2-[4-(2-propynyl)-3-thiosemicarbazone] which crystallises out is filtered of, M.P. 152°.

(b) The 2-propynyl-isothiocyanate required in the case of (a) is prepared as follows:

5.5 g (0.10 Mol) of 2-propynylamine is dissolved in 35 ml of abs. methylene chloride; an addition is then made dropwise at 10°–15°, with stirring, of 7.6 g (0.10 Mol) of carbon disulphide. The reaction mixture is subsequently allowed to warm up to room temperature and is stirred for 30 minutes at this temperature. It is thereupon cooled by means of an ice-water bath to 0°–5°, and a solution of 20.6 g (0.10 Mol) of N,N-dicyclohexylcarbodiimide in 20 ml of abs. methylene chloride added dropwise. The reaction mixture is then allowed to warm up to room temperature and is allowed to stand for 2 hours at this temperature. An amount of 75 ml of pentane is added, and the precipitated 1,3-dicyclohexyl-2-thiourea subsequently separated by filtration with suction. The filtrate is concentrated in a water-jet vacuum with a bath temperature of 20°. The crude 2-propynyl-isothiocyanate is purified by distillation, B.P. 43°–48°/12 Torr.

EXAMPLE 4

27.2 g (0.10 Mol) of 3-(1-methylallyl)-5-methyl-2,4-thiazolidinedione-2-(4-methyl-3-thiosemicarbazone) and 10.1 g (0.11 Mol) of glyoxylic acid hydrate are refluxed in 300 ml of benzene for 60 minutes with stirring and with the use of a water separator. After 15 minutes, 3.5 ml of water has already been separated. The hot reaction solution is subsequently decanted from a small amount of a yellow greasy substance, and is allowed to slowly cool. The 2,2'-azine of 3-(1-methylallyl)-5-methyl-2,4-thiazolidinedione and of 3-methyl-5-hydroxy-2,4-thiazolidinedione which has crystallised out is filtered off under suction, washed with 100 ml of ether, and recrystallised from methylene chloride/hexane, M.P. 141°–143°.

The whole filtrate is washed twice with 50 ml of water each time, dried over sodium sulphate, and concentrated by evaporation. From the slightly yellowish, viscous oil remaining behind, 1 g is separated by preparative layer-chromatography with the aid of 10 PSC finished plates of silica gel 60 F 254 (Merck), 20×20 cm, layer thickness 2 mm, and ether as the eluant. By elution of the most polar zone (Rf ca. 0.3) with 100 ml of chloroform containing 5% of methanol, there is obtaied 1-[[3-(1-methylallyl)-4-oxo-5-methyl-2-thiazolidinylidene]-amino]-3-methyl-5-hydroxy-2-thiohydantoin.

The starting material can be prepared as follows:

(a) 145 g (1 Mol) of 4-(1-methylallyl)-3-thiosemicarbazide, prepared according to G. Pulvermacher and H. Hempel, Ber. 27, 625 (1894), is dissolved in 1000 ml of chloroform, and an addition made at 25°–30°, with stirring and cooling, of 112 g (1.1 Mol) of acetanhydride. The reaction mixture is subsequently refluxed for 2 hours with stirring. It is thereupon cooled in an ice bath to 5°, and 1000 ml of petroleum ether then added. The precipitated 1-acetyl-4-(1-methylallyl)-3-thiosemicarbazide is filtered off under suction, washed with ether, and dried for 20 hours at 70° in a water-jet vacuum, M.P. 132°–133°.

(b) 74 g (0.40 Mol) of 1-acetyl-4-(1-methylallyl)-3-thiosemicarbazide, 68 g (0.445 Mol) of 2-bromopropionic acid and 33 g (0.40 Mol) of anhydrous sodium acetate are refluxed in 400 ml of abs. ethanol for 3 hours with stirring. The reaction mixture is allowed to cool to 20°, and the precipitated inorganic salts are filtered off. The filtrate is concentrated in a water-jet vacuum. The greasy substance remaining is taken up in 250 ml of methylene chloride, and 2N sodium hydroxide solution then added until the pH value is 8. The mixture is well shaken, the methylene chloride solution then separated, and the aqueous phase extracted three times with 100 ml of methylene chloride each time. The combined methylene chloride solutions are dried over 30 g of anhydrous magnesium sulphate. This is subsequently filtered off, and the filtrate concentrated in a water-jet vacuum to obtain 3-(1-methylallyl)-5-methyl-2,4-thiazolidinedione-2-(2-acetyl-hydrazone).

(c) 65.5 g (0.27 Mol) of 3-(1-methylallyl)-5-methyl-2,4-thiazolidinedione-2-(2-acetyl-hydrazone) is dissolved in 200 ml of abs. methanol, and an addition then made at 35°, with stirring, of 120 ml of a 0.67N ethereal hydrochloric acid solution. The reaction mixture is afterwards refluxed for 3 hours, with a fairly thick crystal sludge commencing to precipitate out after one and a half hours. The mixture is then cooled to 5° by means of an ice bath, and 200 ml of petroleum ether (B.P. 40°–60°) added. The precipitated 3-(1-methylallyl)-5-methyl-2,4-thiazolidinedione-2-hydrazone-hydrochloride is filtered off under suction, and subsequently washed with 100 ml of ether.

(d) To liberate the base, 52.4 g (0.222 Mol) of 3-(1-methylallyl)-5-methyl-2,4-thiazolidinedione-2-hydrazone hydrochloride is dissolved in 150 ml of water, and the solution saturated, with ice cooling and stirring, with potassium carbonate. The oil which precipitates is taken up in a mixture of 100 ml of methylene chloride and 100 ml of petroleum ether (B.P. 40°–60°), separated from the aqueous phase, and extracted by shaking with a solution of 25 g of potassium carbonate in 75 ml of water. The organic phase is separated, and concentrated in a water-jet vacuum to obtain 3-(1-methylallyl)-5-methyl-2,4-thiazolidinedione-2-hydrazone in the form of a colourless oil.

(e) 14.1 g (0.071 Mol) of 3-(1-methylallyl)-5-methyl-2,4-thiazolidinedione-2-hydrazone and 5.5 g (0.075 Mol) of methylisothiocyanate are dissolved in 200 ml of methanol, and the solution is refluxed for 2 hours. The methanol is subsequently evaporated off in a water-jet vacuum. The residue is recrystallised twice from chloroform/hexane: the resulting product is 3-(1-methylallyl)-5-methyl-2,4-thiazolidinedione-2-(4-methyl-3-thiosemicarbazone), M.P. 114.5°–115.5°.

EXAMPLE 5

2.04 g (10 mMol) of 1-allyl-6-methyl-2,5-dithiobiurea and 3.25 g (25 mMol) of glyoxylic acid tert. butyl ester are refluxed in 50 ml of benzene for 3 hours with stirring. After cooling, the precipitated 2,2'-azine of 3-methyl-5-hydroxy-2,4-thiazolidinedione and of 3-(2-methylallyl)-5-hydroxy-2,4-thiazolidinedione is filtered off, and washed with benzene. After recrystallisation from isopropanol/chloroform, the substance melts at 200°–203°.

EXAMPLE 6

2.18 g (0.010 Mol) of 1-methyl-6-(2-methylallyl)-2,5-dithiobiurea and 2.03 g (0.022 Mol) of glyoxylic acid hydrate are refluxed in 100 ml of abs. benzene for 2 hours with stirring and with mounted water separator. After cooling, the precipitated 2,2'-azine of 3-methyl-5-hydroxy-2,4-thiazolidinedione and of 3-(2-methylallyl)-5-hydroxy-2,4-thiazolidinedione is filtered off, and subsequently washed with benzene. After recrystallisation from isopropanol/chloroform, the substance melts at 200°–203°.

The following are obtained in an analogous manner:

starting with 2.04 g (0.010 Mol) of 1-allyl-6-methyl-2,5-dithiobiurea, 2,2'-azine of 3-methyl-5-hydroxy-2,4-thiazolidinedione and of 3-allyl-5-hydroxy-2,4-thiazolidinedione, M.P. 170°–171°.

starting with 2.58 g (0.010 Mol) of 1,6-bis-(2-methylallyl)-2,5-dithiobiurea, 2,2'-azine of 3-(2-methylallyl)-5-hydroxy-2,4-thiazolidinedione, M.P. 210°–212°.

EXAMPLE 7

3.0 g (8.7 mMol) of 2,2'-azine of 3-methyl-2,4-thiazolidinedione-1-oxide and of 3-(2-methylallyl)-5-methyl-2,4-thiazolidinedione-1-oxide are stirred in 50 ml of dimethyl sulphoxide and 10 ml of 5N hydrochloric acid for 36 hours at room temperature. There is then added to the reaction mixture 100 ml of water, and the precipitated crude product filtered off with suction. The filter residue is washed with water until neutral, and dried over diphosphorus pentoxide. The crude product is then suspended in 25 ml of methylene chloride, and the insoluble 2,2'-azine of 3-methyl-2,4-thiazolidinedione-1-oxide and of 3-(2-methylallyl)-5-methyl-2,4-thiazolidinedione-1-oxide filtered off. The filtrate is concentrated in vacuo, and thereupon, by the addition of hexane, 2,2'-azine of 3-methyl-5-hydroxy-2,4-thiazolidinedione and of 3-(2-methylallyl)-5-hydroxy-5-methyl-2,4-thiazolidinedione crystallised out, M.P. 120°.

The starting material is prepared as follows:

23.4 g (0.075 Mol) of 2,2′-azine of 3-methyl-2,4-thiazolidinedione and of 3-(2-methylallyl)-5-methyl-2,4-thiazolidinedione is dissolved in 375 ml of acetone and 600 ml of methylene chloride; to the solution there is then added dropwise at 0°–5°, with stirring, a solution of 33.5 g (0.082 Mol) of 87% m-chloroperoxybenzoic acid in 75 ml of acetone. The dropwise addition takes 90 minutes. The reaction mixture is subsequently stirred for 15 hours at room temperature. The precipitated 2,2′-azine of 3-methyl-2,4-thiazolidinedione-1-oxide and of 3-(2-methylallyl)-5-methyl-2,4-thiazolidinedione-1-oxide is filtered off under suction, and then washed twice with 20 ml of methylene chloride each time and three times with 50 ml of ether each time; M.P. 210°–211° (with decomposition).

EXAMPLE 8

0.49 g (1.5 mMol) of 2,2′-azine of 3-methyl-2,4-thiazolidinedione and of 3-(2-methylallyl)-5-methyl-2,4-thiazolidinedione-1-oxide are stirred in 10 ml of dimethyl sulphoxide and 2 ml of 5N hydrochloric acid for 36 hours at room temperature. After treatment of the reaction mixture in a manner analogous to that given in Example 7, 2,2′-azine of 3-methyl-2,4-thiazolidinedione and of 3-(2-methylallyl)-5-hydroxy-5-methyl-2,4-thiazolidinedione is obtained.

The starting material is prepared as follows:

(a) 3.1 g (10 mMol) of 2,2′-azine of 3-methyl-2,4-thiazolidinedione and of 3-(2-methylallyl)-5-methyl-2,4-thiazolidinedione is dissolved in 20 ml of methylene chloride; there is then added dropwise to the solution at 0°–5°, with stirring, a solution of 2.18 g (11 mMol) of 87% m-chloroperoxybenzoic acid in 20 ml of methylene chloride, and the whole stirred for 5 hours at room temperature. The reaction solution is then extracted by shaking twice with 20 ml of 1N sodium carbonate solution each time, and once with 20 ml of water. The methylene chloride solution is evaporated off to leave 3.3 g of crystalline crude product. This is recrystallised once from 50 ml of methanol. For further purification, the resulting product is chromatographed on 50 g of silica gel (0.063–0.20 mesh). The first methylene chloride fractions extract 0.6 g of unmodified 2,2′-azine of 3-methyl-2,4-thiazolidinedione and of 3-(2-methylallyl)-5-methyl-2,4-thiazolidinedione. The subsequent methylene chloride fractions and methylene chloride/1% methanol fractions extract 2,2′-azine of 3-methyl-2,4-thiazolidinedione and of 3-(2-methylallyl)-5-methyl-2,4-thiazolidinedione-1-oxide, which, after a single recrystallisation from methylene chloride/hexane, melts at 204°–206°.

EXAMPLE 9

3.16 g (0.010 Mol) of 2,2′-azine of 3-methyl-5-hydroxy-2,4-thiazolidinedione and of 3-allyl-5-hydroxy-2,4-thiazolidinedione is dissolved in 500 ml of methanol, and the solution refluxed for 3 hours. The methanol is subsequently evaporated off in a water-jet vacuum. The resulting 3-allyl-3′-methyl-5,5′-dihydroxy-2,2′-dithio-1,1′-bihydantoin melts at 181°–183°.

The following are obtained in an analogous manner: from 3.30 g (0.010 Mol) of 2,2′-azine of 3-(2-methylallyl)-5-hydroxy-2,4-thiazolidinedione and of 3-methyl-5-hydroxy-2,4-thiazolidinedione, 3-(2-methylallyl)-3′-methyl-5,5′-dihydroxy-2,2′-dithio-1,1′-bihydantoin; and from 3.70 g (0.010 Mol) of 2,2′-azine of 3-(2-methylallyl)-5-hydroxy-2,4-thiazolidinedione, 3,3′-bis-(2-methylallyl)-5,5′-dihydroxy-2,2′-dithio-1,1′-bihydantoin, M.P. 202°–204°.

What we claim is:

1. A member selected from the group consisting of (1) a compound which is the 2,2′-azine of 3-(2-methylallyl)-5-methyl-2,4-thiazolidinedione and of 3-methyl-5-hydroxy-2,4-thiazolidinedione, (2) a compound which is the 2,2′-azine of 3-(2-methyl-allyl)-5-hydroxy-2,4-thiazolidinedione and of 3-methyl-5-hydroxy-2,4-thiazolidinedione, (3) a compound which is 3-allyl-3′-methyl-5,5′-dihydroxy-2,2′-dithio-1,1′-bi-hydantoin.

2. A compound of claim 1 which is the 2,2′-azine of 3-(2-methyl-allyl)-5-methyl-2,4-thiazolidinedione and of 3-methyl-5-hydroxy-2,4-thiazolidinedione.

3. A compound of claim 1 which is the 2,2′-azine of 3-(2-methyl-allyl)-5-hydroxy-2,4-thiazolidinedione and of 3-methyl-5-hydroxy-2,4-thiazolidinedione.

4. A compound of claim 1 which is 3-allyl-3-methyl-5,5′-dihydroxy-2,2′-dithio-1,1′-bihydantoin.

* * * * *